(12) United States Patent
Hsueh

(10) Patent No.: US 10,034,848 B2
(45) Date of Patent: Jul. 31, 2018

(54) INCREASE OF PROTEIN SYNTHESIS AMELIORATES SYNAPTOPATHY-RELATED NEUROLOGICAL DISORDERS

(71) Applicant: Academia Sinica, Taipei (TW)

(72) Inventor: Yi-Ping Hsueh, Tapei (TW)

(73) Assignee: Academia Sinica, Taipei (TW)

( * ) Notice: Subject to any disclaimer, the term of this patent is extended or adjusted under 35 U.S.C. 154(b) by 24 days.

(21) Appl. No.: 14/925,007

(22) Filed: Oct. 28, 2015

(65) Prior Publication Data

US 2016/0120831 A1    May 5, 2016

Related U.S. Application Data

(60) Provisional application No. 62/074,089, filed on Nov. 3, 2014.

(51) Int. Cl.
*A61K 31/00* (2006.01)
*A61K 31/198* (2006.01)

(52) U.S. Cl.
CPC ............ *A61K 31/198* (2013.01); *A61K 31/00* (2013.01)

(58) Field of Classification Search
None
See application file for complete search history.

(56) References Cited

U.S. PATENT DOCUMENTS

2009/0291928 A1* 11/2009 Nishitani ............. A23L 33/175
514/171
2009/0305945 A1* 12/2009 Wolfram ............. A61K 31/198
514/1.1

OTHER PUBLICATIONS

Cornett et al (Dev Med Child Neurol 57: 733-736, 2015).*
Kimball et al (J Nutr 136: 227S-231S, 2006).*
Wikipedia—Synaptopathy downloaded (https://en.wikipedia.org/wiki/Synaptopathy) on Apr. 27, 2017.*
Morales-Medina et al (J Chem Neuroanat 38: 266-272, 2009).*
Jing et al (Intl J Dev Neurosci 37: 15-20, 2014).*
Crozier et al (J Nutr 135: 376-382, 2005).*
Wang et al (JCI 121: 4820-4837, 2011).*
Summers et al (J Musculoskelet Neuronal Interact 15: 161-170, Jun. 2015).*
Summers et al (J Musculoskelet Neuronal Interact 15: 161-170, Jun. 2015)—abstract.*

* cited by examiner

*Primary Examiner* — Gregory S Emch
*Assistant Examiner* — Aditi Dutt
(74) *Attorney, Agent, or Firm* — Muncy, Geissler, Olds & Lowe, P.C.

(57) ABSTRACT

Disclosed herein is a method for increasing the dendritic spine formation or dendritic spine density in a subject, who is affected by a dendritic spine defect caused by the impairment in neurofibromin (NF1 protein), valosin-containing protein (VCP), atlastin-1 (ATL1), or superoxide dismutase 1 (SOD1). Accordingly, also disclosed herein is a method for treating a subject having or suspected of having a synaptopathy caused by the impairment in NF1, VCP, ATL1, or SOD1.

14 Claims, 14 Drawing Sheets

INCREASE OF PROTEIN SYNTHESIS AMELIORATES SYNAPTOPATHY-RELATED NEUROLOGICAL DISORDERS

BACKGROUND OF THE INVENTION

1. Field of the Invention

The present disclosure in general relates to a method for treating synaptopathy. More particularly, the present disclosure relates to a method for ameliorating the symptom associated with synaptopathy caused by impairment in neurofibromin (NF1 protein), valosin-containing protein (VCP), atlastin-1 (ATL1), or superoxide dismutase 1 (SOD1).

2. Description of Related Art

A dendritic spine is a small membranous protrusion from a neuron's dendrite that typically receives input from a single synapse of an axon. Dendritic spines serve as a storage site for synaptic strength and help transmit electrical signals to the neuron's cell body. Most spines have a bulbous head (the spine head), and a thin neck that connects the head of the spine to the shaft of the dendrite. Spines are very plastic; that is, spines change significantly in shape, volume, and number in small time courses responding to various stimuli. The spine plasticity plays a critical role in perception, cognition, and motivation of a subject. It is known that the impairment in spine morphology and density would affect the motivation or cognitive performance (e.g., learning disability, attention deficit, memory impairment, behavioral difficulty, intellectual disability, impairment in social interaction, or a combination thereof).

Neurofibromin (NF1 protein), encoded by NF1 gene, is a negative regulator of Ras signal transduction pathway and a modulator of adenylyl cyclase pathway. Based on the regulatory role in cell growth and metabolism, mutations in the NF1 gene are associated with various diseases, including tumors (e.g., breast cancer, retinoblastoma, and leukemia), Watson syndrome, and neurofibromatosis type I. Neurofibromatosis type I, a common autosomal dominant disorder, has an incidence of 1 in 3000-4000, half of which are de novo cases. The disease is characterized by progressive neurocutaneous manifestations, including café au lait macules (CALMs), axillary freckling, neurofibromas, and Lisch nodules. Neurofibromatosis type I in children is also frequently associated with cognitive impairments, which are characterized by problems with visuospatial skills, memory, language, executive functioning, and attention. Because of these problems, up to 50-60% and 30-40% of children with Neurofibromatosis type I suffer from learning disabilities and associate with autism spectrum disorders, respectively. Most NF1 children and autism patients need additional support in the form of special education or remedial teaching.

Valosin-containing protein (VCP), encoded by VCP gene and also known as transitional endoplasmic reticulum ATPase (TER ATPase), is a multifunctional AAA (ATPase associated with a variety of cellular activities) protein that functions as a chaperon to control diverse cellular processes. Besides, VCP also functions as an ubiquitin segregase that remodels multimeric protein complexes by extracting polyubiquininated proteins for recycling or promoting degradation by the proteasome. For the implication in widely cellular event, mutations in VCP gene are causative of a pleiotropic degenerative disorder called multisystem proteinopathy (MSP) that can affect muscle, bone and/or the central nervous system. Further, MSP can manifest clinically as frontotemporal dementia (FTD), amyotrophic lateral sclerosis (ALS), autism spectrum disorders (ASDs), inclusion body myopathy (IBM), Paget's disease of bone (PDB), or as a combination of these disorders. Patients suffering from FTD, ALS and ASD usually present with different degrees of cognitive symptoms, such as deficits in social and personal behavior, blunting of emotions, deficits in both expressive and receptive language, and cognitive delays. As of today, few effective treatments are available, most of which merely alleviate the associated symptoms. Accordingly, both patients and their families face the emotional challenges of dealing with the disability and looking ahead to further deterioration.

Superoxide dismutase (also known as superoxide dismutase 1 or SOD1) is an enzyme encoded by SOD1 gene. SOD1 binds copper and zinc ion and is responsible for destroying free superoxide radicals in the body. It is reported that mutations in SOD1 can cause familial amyotrophic lateral sclerosis (ALS), a motor neuron disease that involves the death of neurons and is characterized by stiff muscles, muscle twitching and gradually worsening weakness. The disease usually starts around the age of 60 and in inherited cases around the age of 50. The average survival from onset to death is three to four years, and most die from respiratory failure. To date, there is no effective treatment for ALS.

Atlastin (also known as Atlastin-1), a protein encoded by ATL1 gene, is a dynamin-related GTPase, which plays a role in formation of the tubular endoplasmic reticulum (ER) network and in axon elongation in neurons. It is reported that a heterozygous mutation in ATL1 gene is associated with hereditary spastic paraplegia (HSP), a disease characterized by lower limb spasticity and weakness. Further, HSP is classified as complex or complicated when associated with other neurological signs, including severe amyotrophy, mental retardation, dementia, extrapyramidal signs, deafness or epilepsy, or with extraneurological signs. Nowadays, no specific treatment is known that would prevent, slow, or reverse HSP.

In view of the forging, there exists in the related art a need for an effective method of treating the synaptopathy caused by impairment in NF1, VCP, ATL1, or SOD1 so as to improving the quality of life for patients and their families.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least in part, on the discovery that the impairment in NF1, VCP, ATL1, or SOD1 causes a defect in protein synthesis, which further leads to dendritic spine defect and synaptopathy; and increase of protein synthesis can ameliorate the dendritic spine defects and the symptoms associated with NF1-, VCP-, ATL1-, or SOD1-associated synaptopathy.

Therefore, one aspect of the present disclosure is directed to a method of increasing dendritic spine formation or increasing dendritic spine density in a subject in need thereof; especially, the subject suffering from dendritic spine defects caused by impairment in NF1, VCP, ATL1, or SOD1. The method comprises administering to the subject 0.01 to 1 g/Kg body weight per day of an amino acid having a branched side chain or a pharmaceutically acceptable salt thereof.

Another aspect of the present disclosure pertains to a method for treating a subject having or suspected of having a synaptopathy. According to the embodiments of the present disclosure, the synaptopathy is caused by the impairment in NF1, VCP ATL1, or SOD1. The method comprises administering to the subject 0.01 to 1 g/Kg body weight per day of an amino acid having a branched side chain or a pharmaceutically acceptable salt thereof so as to ameliorate the symptoms associated with the synaptopathy.

According to some embodiments of the present disclosure, the amino acid having a branched side chain or the pharmaceutically acceptable salt thereof increases the protein synthesis in the subject. In the embodiments, the amino acid having a branched side chain or the pharmaceutically acceptable salt thereof ameliorates the dendritic spine defect or the symptoms of synaptopathy caused by the impairment in NF1, VCP ATL1, or SOD1 via increasing the protein synthesis in the subject.

In general, the subject is a human or any other animal subject. According to one embodiment of the present disclosure, the subject is a human.

According to some embodiments of the present disclosure, the amino acid having a branched side chain is selected from the group consisting of, valine, leucine, and isoleucine.

In one specific embodiment, the amino acid having a branched side chain is leucine. According to the specific embodiment, the amount of leucine administered to the subject is about 0.05 to 0.5 g/Kg body weight per day.

According to other embodiments of the present disclosure, the amino acid having a branched side chain is administrated by a route selected from the group consisting of enteral, oral, parenteral, and transmucosal administration, in which the parenteral administration is any of intravenous, intra-arterial, or intraperitoneal injection.

According to one embodiment of the present disclosure, the synaptopathy treatable by the present method can be a motor neuron disease, a neurodevelopmental disorder, or a neurodegenerative disease. Exemplary motor neuron disease includes, but is not limited to, amyotrophic lateral sclerosis (ALS), primary lateral sclerosis (PLS), spinal muscular atrophy (SMA), progressive muscular atrophy (PMA), progressive bulbar palsy (PBP), pseudobulbar palsy, hereditary spastic paraplegia (HSP), Kugelberg-Welander syndrome, Lou Gehrig's disease, Duchenne's paralysis, Werdnig-Hoffmann disease, and benign focal amyotrophy. Neurodevelopmental disorder can be autism spectrum disorder (ASD) or Neurofibromatosis type I. Neurodegenerative disease can be any of Alzheimer's disease (AD), Parkinson disease (PD), Huntington's disease (HD), frontotemporal dementia (FTD), Friedreich's ataxia, age-related macular degeneration, or Creutzfeldt-Jakob disease. In one specific example, the synaptopathy treated by the present method is ALS, HSP and NF1- and VCP-related disorders.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1A:
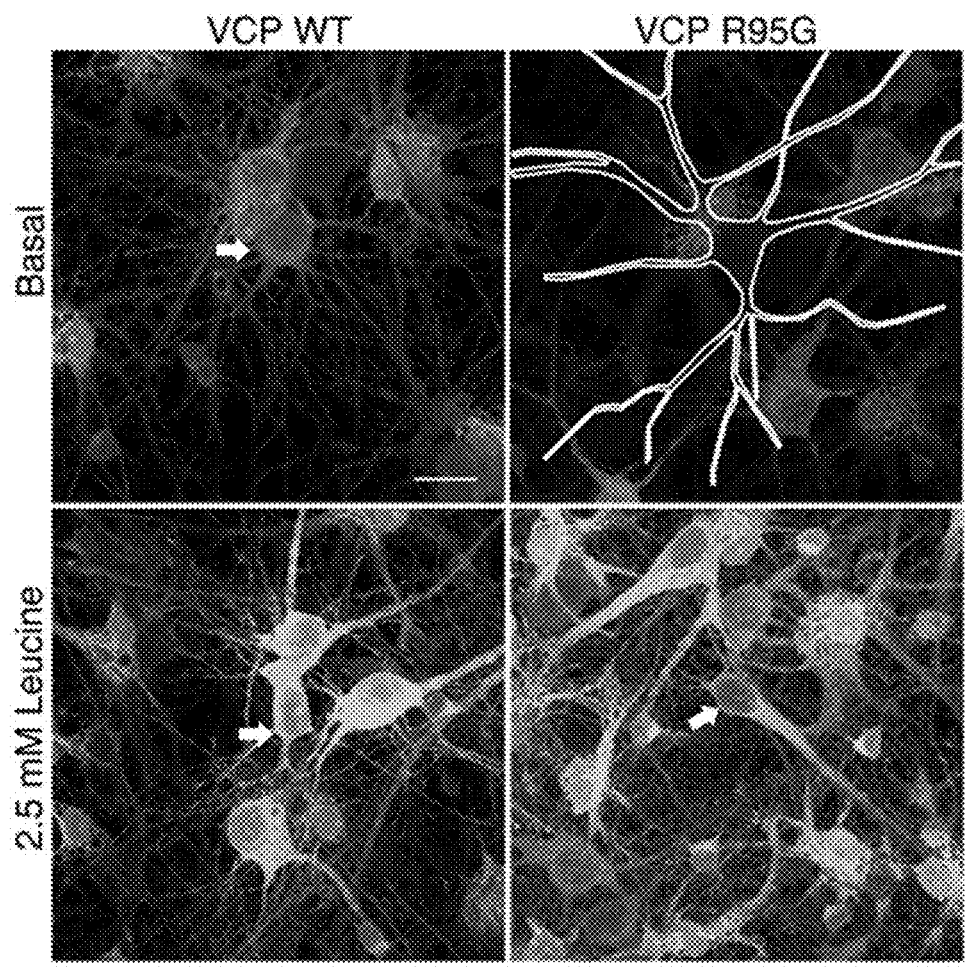
FIG. 1A are confocal microscopy images of neurons that are respectively transfected with specified plasmids respectively expressing wild-type (WT) VCP and mutant VCP, and treated with 2.5 mM leucine for three days and labeled with azidohomoalanine (AHA) for 1 hour according to Example 1 of the present disclosure; the transfected neurons are either pointed by arrows or outlined; scale bar presents 20 μm.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "synaptopathy" used herein comprises a series of diseases that, despite manifesting with different symptoms, have much more in common that the dysfunction of the synapse. The dysfunction of the synapse is associated with numerous neuron diseases, including motor neuron disease, neurodevelopmental disorder and neurodegenerative disease.

The term "neurodevelopmental disorder" used herein refers to any condition, disease, disorder characterized by abnormal neurodevelopment and/or basic biobehavioral processes, including attentional and perceptual processing, executive function, inhibitory control (e.g., sensory gating), social cognition, and communication and affiliative behaviors. Exemplified neurodevelopmental disorders include attention deficit hyperactivity disorder, schizophrenia, obsessive-compulsive disorder, mental retardation, autistic spectrum disorders, cerebral palsy, articulation disorder, and learning disabilities (i.e., reading or arithmetic), verbal or performance aptitude. The term "autism spectrum disorder" or "autistic spectrum disorder" interchangeably refer to a spectrum of neurodevelopmental disorders characterized by impaired social interaction and communication accompanied by repetitive and stereotyped behavior. In the present disclosure, the neurodevelopmental disorder is autism spectrum disorder (ASD) or Neurofibromatosis type I.

The term "motor neuron disease" used herein comprises a group of severe disorders of the nervous system characterized by progressive degeneration of motor neurons (neurons are the basic nerve cells that combine to form nerves). Motor neurons control the behavior of muscles. Motor neuron diseases may affect the upper motor neurons, nerves that lead from the brain to the medulla (a part of the brain stem) or to the spinal cord; or the lower motor neurons, nerves that lead from the spinal cord to the muscles of the body, or both. Spasms and exaggerated reflexes indicate damage to the upper motor neurons. A progressive wasting (atrophy) and weakness of muscles that have lost their nerve supply indicate damage to the lower motor neurons. Examples of motor neuron diseases include, but are not limited to, amyotrophic lateral sclerosis (ALS), primary lateral sclerosis (PLS), spinal muscular atrophy (SMA), progressive muscular atrophy (PMA), progressive bulbar palsy (PBP), pseudobulbar palsy, hereditary spastic paraplegia (HSP), Kugelberg-Welander syndrome, Lou Gehrig's disease, Duchenne's paralysis, Werdnig-Hoffmann disease, and benign focal amyotrophy.

The term "neurodegenerative disease" used herein comprises all diseases accompanied by degeneration of nerve cells, and is not limited by its cause. The neurodegenerative disease in the present invention also includes neuropathy or disease in need of nerve regeneration. The nerve cell may be any type of nerve cells in the living body, including, for example, central nerves (e.g., cerebral nerves and spinal nerves), peripheral nerves (e.g., autonomic nervous system) and so on. In the present disclosure, the neurodegenerative disease can be, for example, Alzheimer's disease (AD), Parkinson disease (PD), Huntington's disease (HD), frontotemporal dementia (FTD), Friedreich's ataxia, age-related macular degeneration, or Creutzfeldt-Jakob disease.

The term "amyotrophic lateral sclerosis" or "ALS" as used herein refers to the group of motor neuron diseases characterized by the loss of motor neurons in the ventral horn of the spinal cord and the cortical neurons that provide their afferent input. ALS includes both the sporadic and familial forms, as well as forms that predominantly affect either the lower motor neurons (e.g., progressive muscular atrophy) and forms that predominantly affect the lower brainstem cranial motor nuclei (e.g., progressive bulbar palsy and bulbar amyotrophic lateral sclerosis).

The term "cognitive disorder" used herein refers to any condition or symptoms characterized by a deficit in mental activities associated with thinking, learning, or memory. Examples of such disorders include agnosias, amnesias, aphasias, apraxias, deliriums, dementias, and learning disorders.

The term "pharmaceutically acceptable salt" as used herein refers to salts which are known to be non-toxic and are commonly used in the pharmaceutical literature. More specifically, the salts retain the biological effectiveness of the present amino acid having a branched side chain and are not biologically or otherwise undesirable. Suitable pharmaceutically acceptable salts include, but are not limited to, metal salts (such as sodium potassium and cesium salts), alkaline earth metal salts (such as calcium and magnesium salts), organic amine salts (such as triethylamine, guanidine and N-substituted guanidine salts), acetamidine, and N-substituted acetamidine, pyridine, picoline, ethanolamine, triethanolamine, dicyclohexylamine, and N,N'-dibenzylethylenediamine salts. Pharmaceutically acceptable salts (of basic nitrogen centers) include, but are not limited to inorganic acid salts (such as the hydrochloride, hydrobromide, sulfate, phosphate), organic acid salts (such as trifluoro acetate and maleate salts), and sulfonates (such as methanesulfonate, ethanesulfonate, benzenesulfonate, p-toluenesulfonate, camphor sulfonate and naphthalenesulfonate).

The term "treatment" is used herein to refer to curative or palliative measure that results in a desired pharmaceutical and/or physiological effect. Preferably, the effect is therapeutic in terms of partially or completely curing synaptopathy. Also, the terms "treatment" and "treating" as used herein refer to application or administration of the amino acid having branched side chain or a pharmaceutically acceptable salt thereof to a subject, who has an synaptopathy, a symptom thereof, a disease or disorder secondary thereto, or a predisposition toward, with the purpose to partially or completely alleviate, ameliorate, relieve, delay onset of, inhibit progression of, reduce severity of, and/or reduce incidence of one or more symptoms or features of the synaptopathy.

The term "effective amount" as used herein refers to the quantity of a component or medicament which is sufficient to yield a desired "effective treatment" as defined hereinabove. The specific therapeutically effective amount will vary with factors such as the particular condition being treated, the physical condition of the patient (e.g., the patient's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects. Effective amount may be expressed, for example, as the total mass of the medicament (e.g., in grams, milligrams or micrograms) or a ratio of mass of the medicament to body mass, e.g., as milligrams per kilogram (mg/kg). Persons having ordinary skills could calculate the human equivalent dose (HED) for the medicament (such as the present amino acid having a branched side chain or the pharmaceutically acceptable salt thereof) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

As known by a skilled artisan, genetically encoded amino acids are generally divided into families: (1) acidic amino acid, which includes aspartate and glutamate; (2) basic amino acid, which includes lysine, arginine, and histidine; (3) amino acid with polar uncharged side chain, which includes glycine, cysteine, serine, threonine, asparagine, and glutamine; and (4) amino acid with branched side chain, which includes alanine, valine, leucine, proline, isoleucine, methionine, phenylalanine, tyrosine, and tryptophan. The present invention unexpectedly discovers that three amino acids with branched side chain are useful in treating the synaptopathy via ameliorating the dendritic spine defect caused by impairment in NF1, VCP, ATL1, or SOD1.

The term "subject" refers to a mammal including the human species that is treatable with methods of the present invention. The term "subject" is intended to refer to both the male and female gender unless one gender is specifically indicated.

As the need for safely and efficiently ameliorating the conditions associated with the synaptopathy caused by impairment in NF1, VCP, ATL1, or SOD1, and accordingly, rendering the patients and their families a better quality of life, the objective of the present disclosure aims at providing a method for treating a subject in need thereof.

The present disclosure unexpectedly discovers that the impairment in NF1, VCP, ATL1, or SOD1 causes a defect of protein synthesis in a subject. According to the present invention, the defect of protein synthesis would further lead to dendritic spine defect and synaptopathy. Based on the discovery, the present disclosure provides a novel method of increasing the protein synthesis, and thus, ameliorating the dendritic spine defects and the symptoms associated with synaptopathy caused by the impairment in NF1, VCP, ATL1, or SOD1.

One aspect of the present disclosure is directed to a method useful in increasing dendritic spine formation or increasing dendritic spine density in the subject in need thereof; more specifically, the subject is affected by dendritic spine defects caused by impairment in NF1, VCP, ATL1, or SOD1. The method comprises administering to the subject a therapeutically effective amount of an amino acid having a branched side chain or a pharmaceutically acceptable salt thereof so as to increase dendritic spine formation or increase dendritic spine density in the subject.

According to some embodiments of the present disclosure, the amino acid having a branched side chain or the pharmaceutically acceptable salt thereof increases the protein synthesis in the subject. In the embodiments, the amino acid having a branched side chain or the pharmaceutically acceptable salt thereof ameliorates the dendritic spine defect caused by impairment in NF1, VCP, ATL1, or SOD1 via increasing the protein synthesis in the subject.

According to other embodiments of the present disclosure, the amino acid having a branched side chain can be any of valine, leucine, or isoleucine.

In one embodiment, the subject is a mouse. To elicit a therapeutic effect on mice, the therapeutically effective amount is about 0.12 to 12.5 g/Kg per day. In one preferred example, the amino acid having a branched side chain is leucine, and the therapeutically effective amount of leucine is about 0.6 to 6 g/Kg per day.

A skilled artisan could calculate the human equivalent dose (HED) for the present amino acid with a branched side chain, based on the doses determined from animal models. Accordingly, the therapeutically effective amount is about 0.01 to 1 g/Kg per day for human; for example, the therapeutically effective amount can be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 g/Kg per day. In one preferred example, the amino acid having a branched side chain is leucine, and the therapeutically effective amount of leucine is about 0.05 to 0.5 g/Kg per day.

In one specific example, the therapeutically effective amount of leucine is about 0.9 to 3.6 g/Kg per day for mice, about 0.073 to 0.292 g/Kg per day for adults, and about 0.108 to 0.432 g/Kg per day for children.

In the embodiment of the present disclosure, the amino acid having a branched side chain may be administered by a route selected from the group consisting of enteral, oral, parenteral, and transmucosal administration, in which the parenteral administration is any of intravenous, intra-arterial, or intraperitoneal injection. According to one working example of the present disclosure, the amino acid having a branched side chain is treated through oral administration.

As introduced above, dendritic spine is associated with the motivation and cognition of a subject, and the impairment in spine morphology and density would cause disorders of motivation (i.e., abnormality or deficiency in motivation) and cognition (e.g., memory impairment and learning disability), both of which disturb the lives of patients and their families. Accordingly, it is the second aspect of the present disclosure to provide a method for treating a synaptopathy associated with dendritic spine defects. Specifically, the method is useful in treating a subject having or suspected of having a synaptopathy. According to the embodiments of the present disclosure, the synaptopathy is caused by the impairment in NF1, VCP, ATL1, or SOD1. The method comprises administering to the subject 0.01 to 1 g/Kg body weight per day of an amino acid having a branched side chain or a pharmaceutically acceptable salt thereof so as to ameliorate his/her symptoms associated with the synaptopathy.

According to the embodiments of the present disclosure, the amino acid having a branched side chain or the pharmaceutically acceptable salt thereof increases the protein synthesis in the subject. In the embodiments, the amino acid having a branched side chain or the pharmaceutically acceptable salt thereof ameliorates the symptoms associated with the synaptopathy caused by impairment in NF1, VCP, ATL1, or SOD1 via increasing the protein synthesis in the subject.

In general, the subject suitable to accept the method of the present disclosure includes, but is not limited to, a human, a mouse, and any other animal subject. According to the preferred embodiment, the subject is a human.

The synaptopathy associated with dendritic spine defects can be a motor neuron disease, a neurodevelopmental disorder, or a neurodegenerative disease. According to one embodiment of the present disclosure, the motor neuron disease treatable by the present disclosure includes, but is not limited to, amyotrophic lateral sclerosis (ALS), primary lateral sclerosis (PLS), spinal muscular atrophy (SMA), progressive muscular atrophy (PMA), progressive bulbar palsy (PBP), pseudobulbar palsy, hereditary spastic paraplegia (HSP), Kugelberg-Welander syndrome, Lou Gehrig's disease, Duchenne's paralysis, Werdnig-Hoffmann disease, and benign focal amyotrophy. According to another embodiment of the present disclosure, the neurodevelopmental disorder is autism spectrum disorder (ASD) or Neurofibromatosis type I. According to still another embodiment of the present disclosure, the neurodegenerative disease can be any of Alzheimer's disease (AD), Parkinson disease (PD), Huntington's disease (HD), frontotemporal dementia (FTD), Friedreich's ataxia, age-related macular degeneration, or Creutzfeldt-Jakob disease.

According to one embodiment of the present disclosure, the present method possesses a therapeutic effect on ALS. In the embodiment, the present method can significantly prolong the survival time of the subject having ALS.

According to another embodiment of the present disclosure, the present method is employed to treat a subject having a neurodegenerative disease. In the embodiment, the subject having a neurodegenerative disease is present with cognitive symptoms, for example, memory impairment and learning disability; and the method is useful in improving the memory or learning ability. It is noted that the method of the present disclosure is not limited thereto. For example, the cognitive symptoms ameliorated by the present method further comprise attention deficit, behavioral difficulty, intellectual disability, or impairment in social interaction.

As to efficiently treat the subject with a synaptopathy caused by impairment in NF1, VCP, ATL1, or SOD1, the amount of amino acid having a branched side chain administered to the subject is about 0.01 to 1 g/Kg body weight per day. In the embodiments of the present disclosure, the amino acid having a branched side chain can be any of valine, leucine, or isoleucine. In one preferred example, the amino acid having a branched side chain is leucine, and the amount of leucine administered to the subject is about 0.05 to 0.5 g/Kg body weight per day.

As would be appreciated, in addition to the amino acids described above, other substances that increase the protein synthesis can also achieve the therapeutic effect on synaptopathy.

In certain embodiments, the amino acid having a branched side chain is given to the subject via a route selected from the group consisting of enteral, oral, parenteral, and transmucosal administration, in which the parenteral administration is any of intravenous, intra-arterial, or intraperitoneal injection. According to one of the working examples, the amino acid having a branched side chain is administrated through oral administration.

As would be appreciated, in addition to the amino acid with a branched side chain or a pharmaceutically acceptable salt thereof as described above, the subject having a synaptopathy may be concurrently or simultaneously treated with other active ingredients. The active ingredient can be an approved agent, a clinical agent, or an agent undergoing clinical trials. For example, the agent used to ameliorate the symptoms associated with motor neuron disease may be selected from the group consisting of Riluzole, GSK1223249 (Ozanezumab), NP001, Neuralstem, Brainstorm, Arimoclomol (CytRx), sNN0029, GM604, Tirasemtiv (CK-2017357), ISIS SOD1Rx, Memantine, and Dexpramipexole. Suitable agent used to ameliorate the symptoms associated with neurodegenerative disease includes, but is not limited to, Aricept (donepezil), Razadyne (galantamine), Namenda (memantine), Exelon (rivastigmine), and Namzaric (donepezil and memantine).

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Animal

Nf1$^{+/-}$ and SOD1-G93A mice were purchased from the Jackson Laboratory and maintained by backcrossing to C57BL/6 mice. All animals were kept in an air-conditioned animal shelter at room temperature of 22° C. to 24° C. with controlled level of humidity (40% to 50%) in a 12-hour light-dark cycle. The experiments were approved by the Academia Sinica Institutional Animal Care and Utilization Committee (Taipei, Taiwan, R.O.C.).

Cell Culture

For primary neuronal culture, pregnant mice were sacrificed by subjecting to $CO_2$ inhalation, and the fetal pups were isolated and sacrificed by decapitation. Then, cortical neurons were dissociated from the brains of embryonic mice of 18 days. The obtained neurons were cultured in Neurobasal medium, supplemented with 2% B27 supplement, 0.5 mM glutamine, and 12.5 µM glutamate in the density of 260,000 cells/cm$^2$. The cells were kept in a 5% $CO_2$- humidified chamber at 37° C.

$VCP^{R95G}$ Plasmid

The wild-type VCP gene was amplified by PCR using a forward primer having a nucleotide sequence of SEQ ID NO: 1, and a reverse primer having a nucleotide sequence of SEQ ID NO: 2. The amplified DNA segment was subsequently constructed in to GW1-Myc plasmid. To generate the R95G mutation, a pair of primers respectively having nucleotide sequences of SEQ ID NOs: 3 and 4 were used in site-directed mutagenesis with wild-type VCP construct as a template.

ATL-1 Plasmid

Mouse Atl1 was amplified by PCR with a primer set respectively having nucleotide sequences of SEQ ID NOs: 5 and 6. The amplified products were subcloned into the Gw1-Myc2b vector. The R217Q mutant was generated by site directed mutagenesis with a primer set respectively having nucleotide sequences of SEQ ID NOs: 7 and 8.

Analysis of Dendritic Spine Formation and Density

Neurons were seeding on coverslips coated with poly-L-lysine. Plasmid DNA expressing wild-type (i.e., $VCP^{WT}$) or mutant VCP (i.e., $VCP^{R95G}$) were respectively transfected with calcium phosphate into the neurons, which were cultured in a cultured medium with or without (designated as Basal) leucine (2.5 mM as the final concentration in the cultured medium). Three days post-transfection, the transfected neurons were washed twice with PBS, and then fixed with 4% paraformaldehyde.

Images of neurons were recorded with a confocal microscope (LSM700, Zeiss) equipped with a Plan-Apochromat 63×NA 1.4 oil objective lens (Zeiss) and captured with Zen acquisition and analysis software (Zeiss) at 20-22° C. as a Z-series of 5-12 sections spaced 0.6-0.8 µm apart. The Z-series was then projected into single images. The images were processed with Photoshop (Adobe), with minimal adjustment of brightness or contrast applied to the whole images.

To analyze dendritic spine density, the spine number of each dendrite fragment about 20 µm in length, which started from a point 20 µm away from the soma, was manually counted using Image J software. As dendritic spine formation is highly sensitive to culture conditions, each experiment was repeated using the same lot of culture medium. The data from independent experiments were pooled for statistical analysis only when the variation of the control group was not significantly different between repeated experiments. To minimize the effects of bias, some of the critical experiments were performed blind by relabeling the samples with the assistance of other lab members.

Contextual Fear Conditioning

To examine the effect of leucine on contextual fear memory, mice (wild-type or Nf1$^{+/-}$ mice) were provided with normal water or leucine supplement water (0.9-3.6 g/Kg) for 7 days prior to testing, which was continued through the entire behavioral task. Mice were subjected to contextual fear conditioning, which was carried out for 6 days with one trial per day. For the first 5 days, mice were placed into the conditioning chamber for 60 sec, then a single foot shock was performed (0.4 mA intensity for 2 sec). After the foot shock, mice were left in the chamber for another 120 sec before returning to their home cage. On the 6$^{th}$ day, mice were placed into the conditioning chamber for 180 sec without foot shock. Freezing responses during the first 10-60 sec of each trial were videotaped and measured using the FreezeScan 2.0 system (CleverSys).

Animal Model of Amyotrophic Lateral Sclerosis (ALS)

To examine the effect of leucine on ALS, 120 days old mice (wild-type or SOD1-G93A mice) were provided with normal water or leucine supplement water (80 mg/day) until animal died.

Statistical Analysis

All the quantitative data in the present disclosure were presented as means plus SEM or cumulative distribution. Graphs were plotted using GraphPad Prism 5.0 (GraphPad software). For dendritic spine analysis, three dendrites of each neuron were quantitated. Data collection and analysis were conducted randomly and most experiments (except the mouse behavior test) were blind. Two-way ANOVA with Bonferroni's test were performed using SigmaStat 3.5. For cumulative probability distributions of spine density, the statistical analysis was analyzed with Kolmogorov-Smirnov test (SPSS software, version 10.0, SPSS, Chicago, Ill.). P values of less than 0.05 were considered significant.

Example 1 Effect of Leucine on Dendritic Spine Formation

Figure 1B:
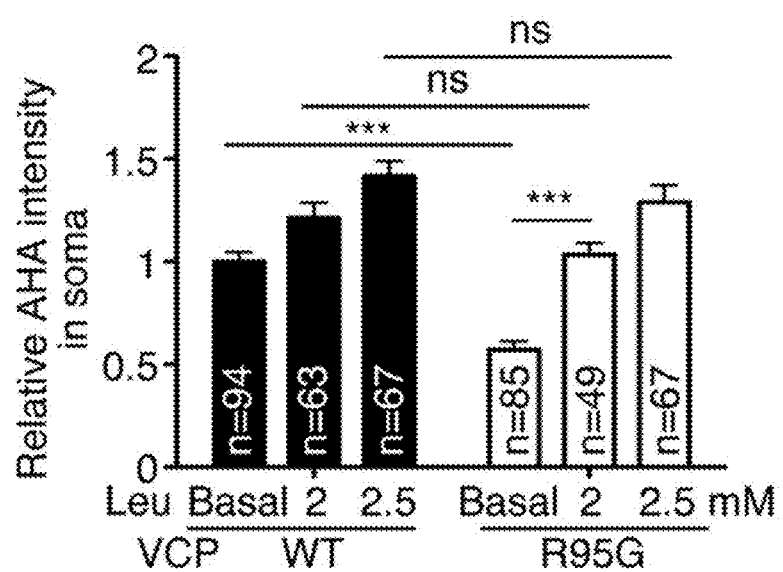
FIG. 1B is a histogram depicting the relative AHA intensity of neurons that were respectively transfected with specified plasmids, and treated with different concentrations of leucine for three days and labeled with AHA for 1 hour according to Example 1 of the present disclosure; data from three independent experiments are presented as mean plus standard error of mean (SEM); ns, no significance; ***, $P<0.001$.
Figure 1C:
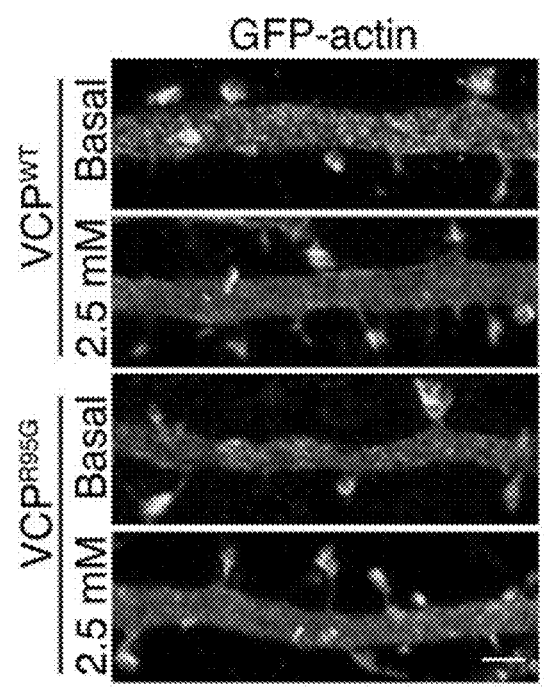
FIG. 1C are confocal microscopy images of neurons that are respectively transfected with specified plasmids respectively expressing WT VCP and mutant VCP, and treated with 2.5 mM leucine for three days according to Example 1 of the present disclosure; scale bar presents 2 μm.
Figure 1D:
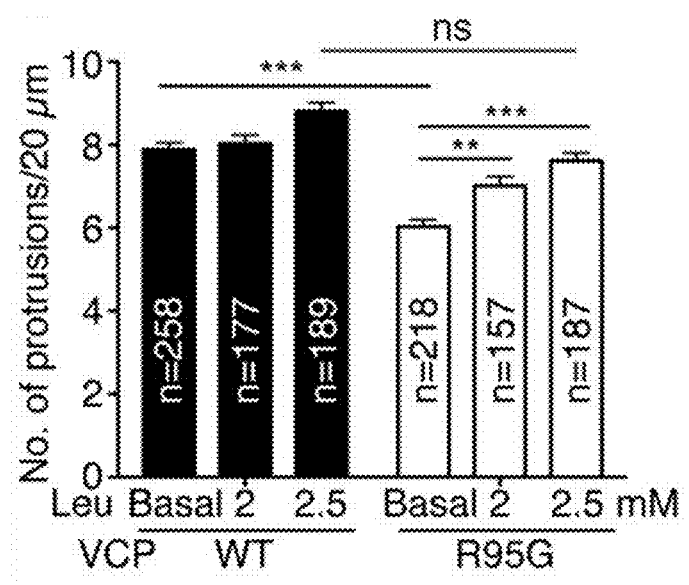
FIG. 1D is a histogram depicting the dendritic spine density of neurons that were respectively transfected with specified plasmids and treated with different concentrations of leucine for three days according to Example 1 of the present disclosure; data from three independent experiments are presented as mean plus standard error of mean (SEM); ns, no significance; , $P<0.01$; *, $P<0.001$.

To evaluate the effect of leucine on dendritic spine formation or density, neurons transfected with plasmids that respectively expressed wild-type VCP ($VCP^{WT}$) and mutant VCP ($VCP^{R95G}$) were incubated in a cultural medium in the regular concentration (0.8 mM) of leucine or presence of final 2.5 mM leucine for 3 days. As the data of FIGS. 1A and 1B, compared with $VCP^{WT}$-expressing neurons, VCP mutation significantly decreased AHA intensity in neurons (*, P<0.001); and the treatment of leucine dose-dependently increased the AHA intensity in $VCP^{R95G}$-neurons to the level comparable to neurons expressing WT VCP. FIG. 1C are the representative images of dendrite fragments of those neurons. As calculated in FIG. 1D, compared with the $VCP^{WT}$-expressing dendrite fragment, $VCP^{R95G}$-expressing dendrite fragment had a lower number of protrusions (*, P<0.001). While adding leucine did not produce obvious effect on the $VCP^{WT}$-dendrite fragment, leucine significantly increased the protrusion number of $VCP^{R95G}$-dendrite fragment in a dose-dependent manner (, P<0.01 between basal and 2 mM; *, P<0.001 between basal and 2.5 mM).

Figure 2A:
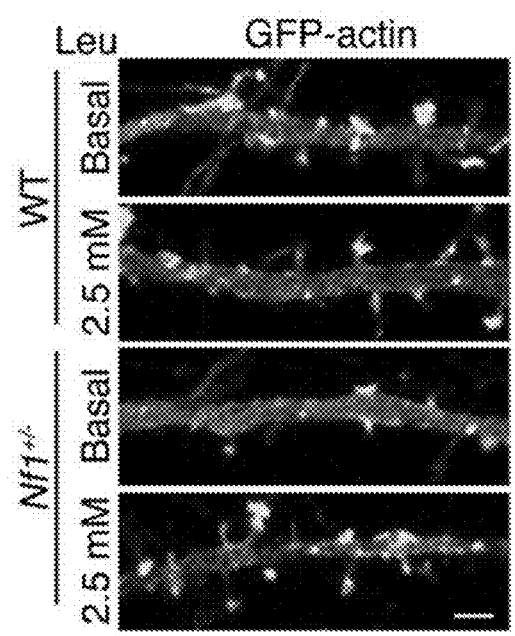
FIG. 2A are confocal microscopy images of wild-type or NF1 heterozygous (NF1$^{-/+}$) neurons that are respectively treated with different concentrations of leucine for three days according to Example 1 of the present disclosure; scale bar presents 2 μm.
Figure 2B:
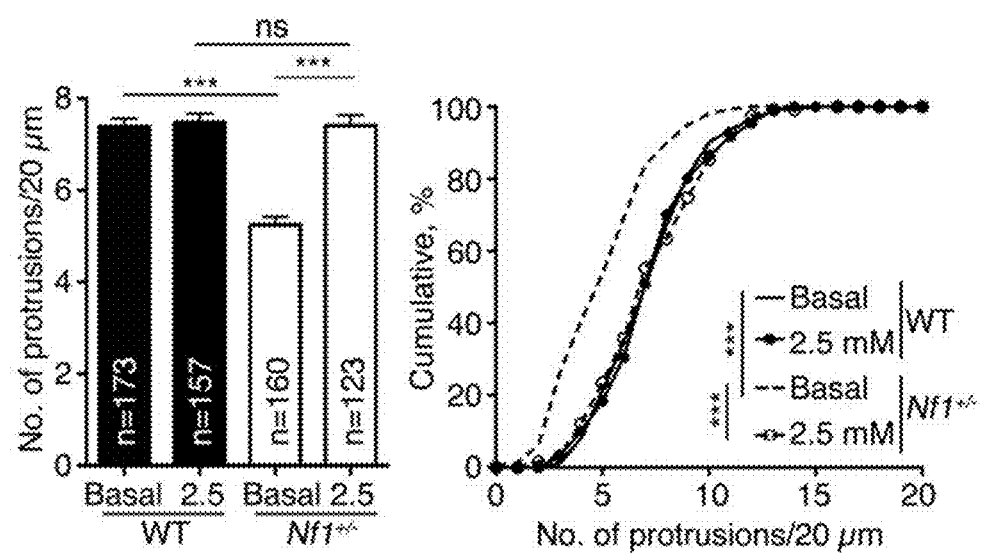
FIG. 2B are a histogram and a curve chart depicting the dendritic spine density of wild-type or NF1$^{-/+}$ neurons that are respectively treated with different concentrations of leucine for three days according to Example 1 of the present disclosure; data from three independent experiments are presented as mean plus SEM; ns, no significance; ***, $P<0.001$.

With a similar result, the dendrite fragments of neurons dissociated from Nf1$^{+/-}$ mice had a lower protrusion number than those dissociated from wild-type mice (***, P<0.001, FIGS. 2A and 2B). The presence of leucine did not further raise the number of protrusions in wild-type dendrite fragment. However, addition of leucine significantly ameliorated the defect in dendritic spine formation caused by NF1 impairment (FIG. 2A), and thus, increased the dendritic spine number (FIG. 2B). Surprisingly, the protrusion number of Nf1$^{+/-}$ neurons treated with 2.5 mM leucine was equal to that of wild-type neurons, and there was no statistical difference between the two groups.

Figure 3:
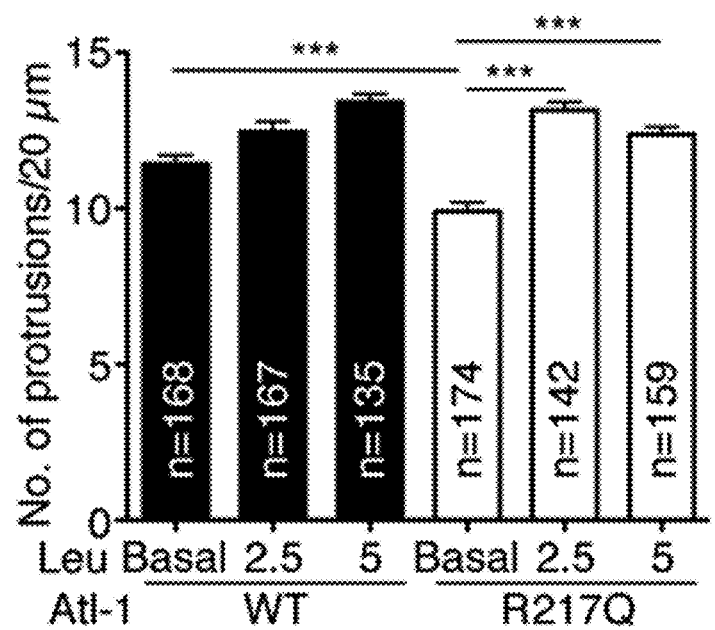
FIG. 3 is a histogram depicting the dendritic spine density of neurons that were respectively transfected with specified plasmids and treated with different concentrations of leucine for three days according to Example 1 of the present disclosure; data from three independent experiments are presented as mean plus standard error of mean (SEM); ***, $P<0.001$.

The effect of leucine on dendritic spine formation or density was further confirmed in the cells respectively expressed wild-type ATL1 (ATL-1$^{WT}$) and mutant ATL1 (ATL-1$^{R95G}$). FIG. 3 illustrated that compared with ATL-1$^{WT}$, ATL-1$^{R95G}$ had a lower number of protrusions (*, P<0.001). The treatment of 2.5 mM or 5 mM leucine significantly increased the dendritic spine number (*, P<0.001).

These data indicated that impairment in NF1, VCP, or ATL1 caused a defect in the protein synthesis and the dendritic spine formation; and administering leucine could effectively promote the dendritic spine formation via increasing protein synthesis, and thus, restore the dendritic spine density to normal levels.

Example 2 Effect of Leucine on Cognitive Disorder

Figure 4A:
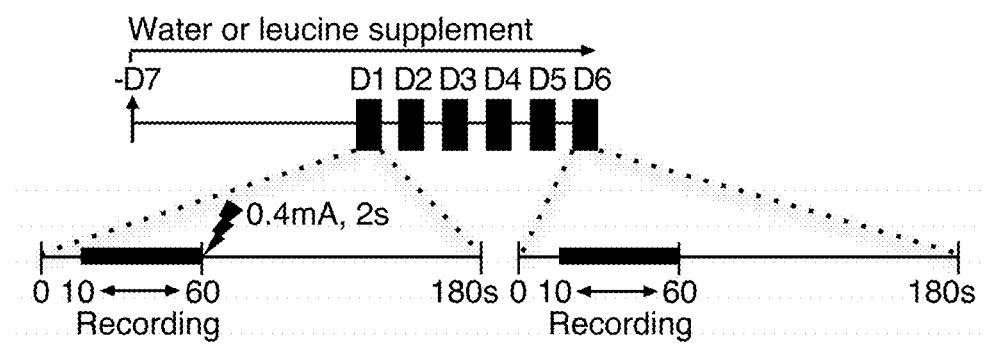
FIG. 4A is a schematic diagram depicting the protocol of administration of water or leucine solution, and assessment of contextual fear conditioning according to Example 2 of the present disclosure.
Figure 4B:
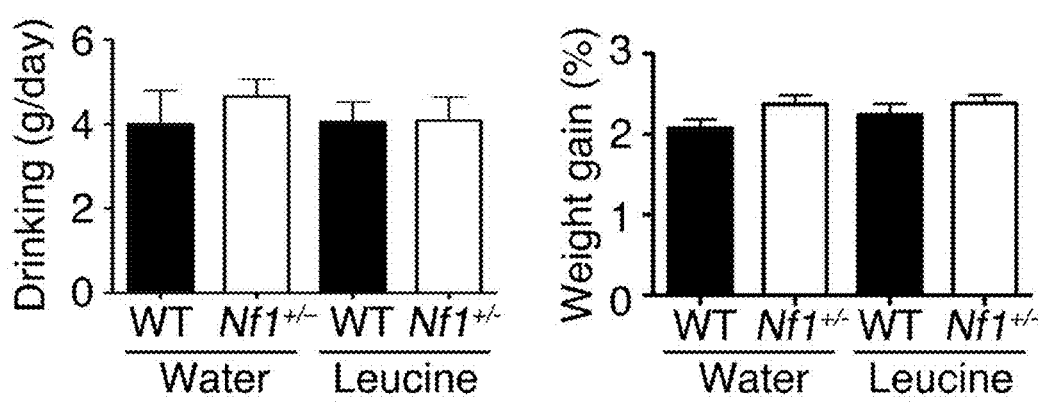
FIG. 4B is a histogram depicting the average daily amounts of water or leucine ingested (left panel), and the net gain of body weight at day 6 of the protocol of the present disclosure (right panel)

Nf1$^{+/-}$ mice were used to study the effect of leucine on learning and memory, in which the effect was assessed by contextual fear conditioning as described in Materials and Methods. Briefly, wild-type or Nf1$^{+/-}$ mice were administered water or leucine, as a supplement in water, for 7 days and then subjected to contextual fear conditioning (FIG. 4A). There was no difference in drinking preference for water or leucine solution between WT and Nf1$^{+/-}$ mice, nor was there difference in weight gain between the two mice (FIG. 4B).

Figure 4C:
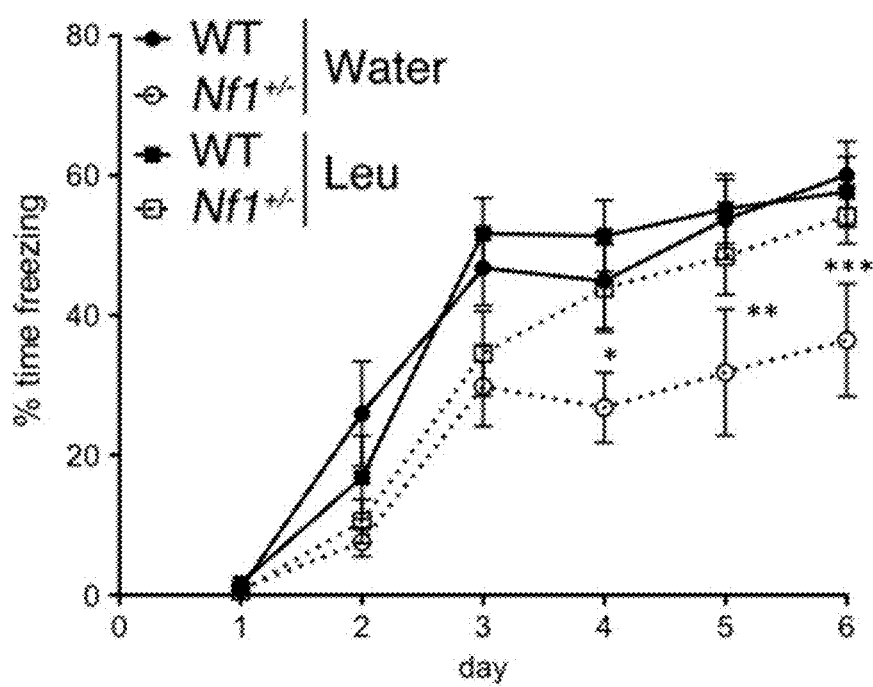
FIG. 4C is a line chart depicting daily fear responses of mice, in which the responses are assessed by contextual fear conditioning and presented as percentage of time freezing (% time freezing) according to Example 2 of the present disclosure.
Figure 4D:
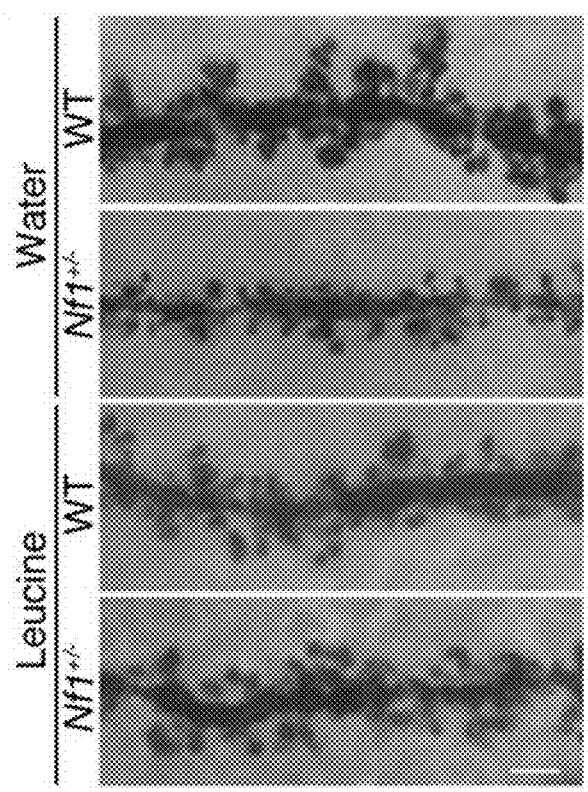
FIG. 4D is a representative image of neurons under confocal microscopy, in which the neurons are isolated from the brains of wild-type and NF1$^{-/+}$ mice that are administrated with water or leucine solution according to Example 2 of the present disclosure; scale bar presents 2 μm.
Figure 4E:
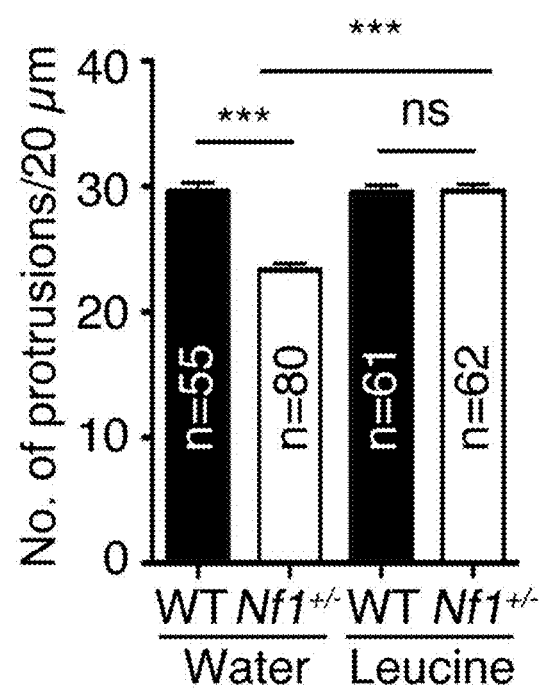
FIG. 4E is a histogram depicting the dendritic spine number of neurons isolated from the brains of wild-type or NF1$^{-/+}$ mice, which are administrated with water or leucine solution according to Example 2 of the present disclosure; data from three independent experiments are presented as mean plus SEM; ns, no significance; ***, $P<0.001$.

In the assessment of contextual fear conditioning, the time freezing of wild-type mice was higher than 40% from day 3 (FIG. 4C). Comparatively, Nf1$^{+/-}$ mice exhibited a reduced freezing response, which was lower than 40% during the entire task. While leucine supplement did not further enhance the fear memory in wild-type mice, it is worth noting that leucine could significantly increase the associative memory of Nf1$^{+/-}$ mice, and after administration, the freezing responses of Nf1$^{+/-}$ mice were comparable to those of WT mice. Golgi staining of mouse brains also revealed an increase in dendritic spine density in Nf1$^{+/-}$ mice after taking leucine solution (FIGS. 4D and 4E).

The data suggested that leucine can effectively ameliorate the defects in memory and learning in Nf1$^{+/-}$ mice via restoring their dendritic spine densities.

Example 3 Effect of Leucine on ALS

Figure 5A:
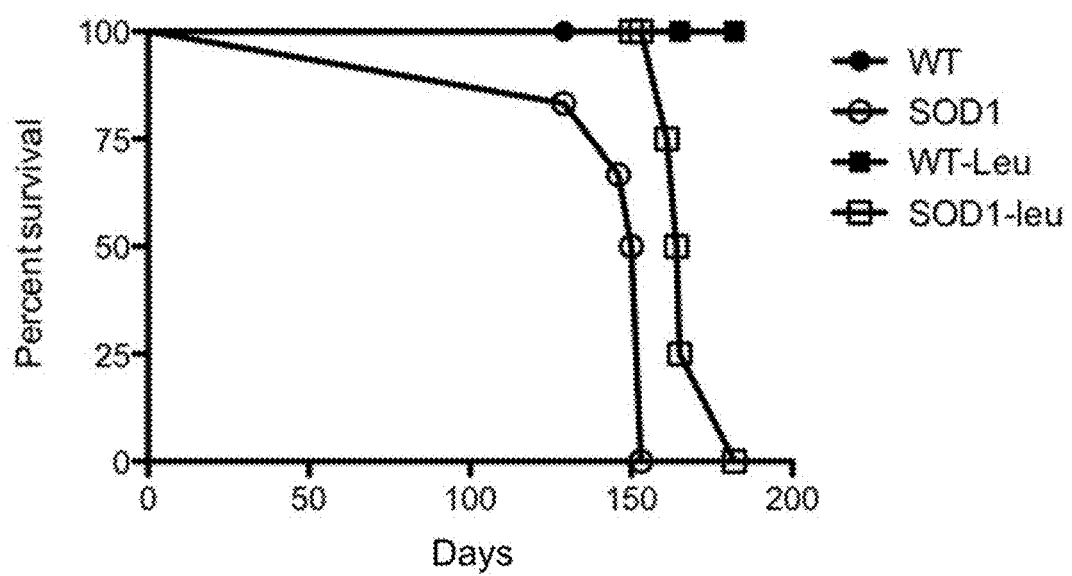
FIG. 5A is a line chart depicting the survival percentage of WT and SOD1 mutant mice treated with or without leucine according to Example 3 of the present disclosure.
Figure 5B:
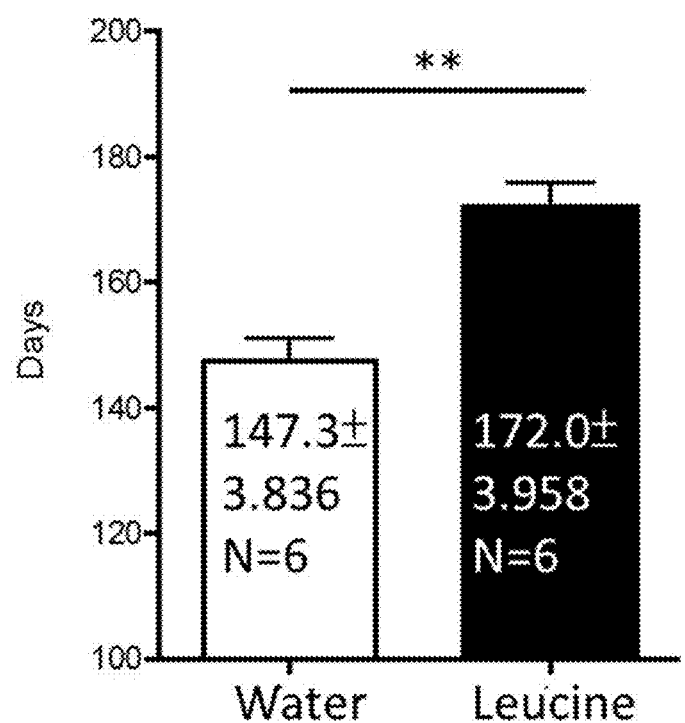
FIG. 5B is a histogram depicting the mean survival time of SOD1 mutant mice treated with or without leucine according to Example 3 of the present disclosure.

SOD1-G93A mouse is an animal model widely used in the art for ALS study. In this example, the SOD1-G93A transgenic mice were used to evaluate the effect of leucine on ALS. As depicted in FIG. 5A, compared to the wild-type mice, dying of SOD1-G93A mice began on day 129, and the survival curve declined steeply to zero on day 153. Administration of leucine supplement significantly increased the percentage of survival SOD1-G93A mice, in which the mean survival time of SOD1-G93A control mice was 147.3±3.84 days, while that of leucine treated SOD1-G93A mice was 172.0±3.96 days (FIG. 5B).

The data indicated that leucine can significantly prolong the survival time of SOD1-G93A mice.

In conclusion, the present disclosure provides a method for ameliorating dendritic spine defects caused by the impairment in NF1, VCP, ATL1, or SOD1 through increasing the dendritic spine formation and restoring the dendritic spine density. Accordingly, the present disclosure also provides a method useful in treating a subject suffering from a NF1-, VCP-, or SOD1-associated synaptopathy. Thus, the present disclosure confers a safely and effectively therapeutic effect on a subject with defect of NF1, VCP, ATL1, or SOD1 so as to greatly improve his/her quality of life.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of increasing dendritic spine formation or increasing dendritic spine density in a subject, consisting of administering to the subject 0.01 to 1 g/Kg body weight per day of a leucine or a pharmaceutically acceptable salt thereof as the sole active ingredient, wherein the subject suffers from a dendritic spine defect caused by impairment in neurofibromin (NF1 protein), and the administration of 0.01 to 1 g/Kg body weight per day of the leucine or the pharmaceutically acceptable salt thereof increases dendritic spine formation or increases dendritic spine density in the subject.

2. The method of claim 1, wherein the leucine or the pharmaceutically acceptable salt thereof increases a protein synthesis in the subject.

3. The method of claim 1, wherein the leucine or the pharmaceutically acceptable salt thereof ameliorates a dendritic spine defect caused by impairment in NF1 via increasing a protein synthesis in the subject.

4. The method of claim 1, wherein the leucine is administered to the subject in the amount of about 0.05 to 0.5 g/Kg body weight per day.

5. The method of claim 1, wherein the subject is a human.

6. The method of claim 1, wherein the leucine is administrated to the subject by a route selected from the group consisting of enteral, oral, transmucosal, intravenous, intra-arterial, and intraperitoneal injection.

7. A method for treating a subject having or suspected of having a synaptopathy, consisting of administering to the subject 0.01 to 1 g/Kg body weight per day of a leucine or a pharmaceutically acceptable salt thereof as the sole active ingredient, wherein
the administration of 0.01 to 1 g/Kg body weight per day of the leucine or the pharmaceutically acceptable salt thereof ameliorates the symptoms associated with the synaptopathy, and
the synaptopathy is caused by impairment in NF1.

8. The method of claim 7, wherein the leucine or the pharmaceutically acceptable salt thereof increases a protein synthesis in the subject.

9. The method of claim 7, wherein the leucine or the pharmaceutically acceptable salt thereof ameliorates the symptoms associated with the synaptopathy caused by impairment in NF1 via increasing a protein synthesis in the subject.

10. The method of claim 7, wherein the synaptopathy is a neurodevelopmental disorder.

11. The method of claim 10, wherein the neurodevelopmental disorder is Neurofibromatosis type I.

12. The method of claim 7, wherein the leucine is administered to the subject in the amount of about 0.05 to 0.5 g/Kg body weight per day.

13. The method of claim 7, wherein the subject is a human.

14. The method of claim 7, wherein the leucine is administrated by a route selected from the group consisting of enteral, oral, transmucosal, intravenous, intra-arterial, and intraperitoneal injection.

* * * * *

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: VCP primer-F

<400> SEQUENCE: 1
ggggtaccgc ctctggagcc gattcaa                               27

<210> SEQ ID NO 2
<211> LENGTH: 32
<212> TYPE: DNA
<213> ORGANISM: Artificial Sequence
<220> FEATURE:
<223> OTHER INFORMATION: VCP primer-R

<400> SEQUENCE: 2
gaagatcttt agccatacag gtcatcgtca tt                         32

<210> SEQ ID NO 3

```
<211> LENGTH: 41
<212> TYPE: DNA
<213> ORGANISM: Artificial Sequence
<220> FEATURE:
<223> OTHER INFORMATION: VCP mutation-F

<400> SEQUENCE: 3
ttcggaataa cctccgagtt ggcctaggag atgtcatcag c                          41

<210> SEQ ID NO 4
<211> LENGTH: 41
<212> TYPE: DNA
<213> ORGANISM: Artificial Sequence
<220> FEATURE:
<223> OTHER INFORMATION: VCP mutation-R

<400> SEQUENCE: 4
gctgatgaca tctcctaggc caactcggag gttattccga a                          41

<210> SEQ ID NO 5
<211> LENGTH: 28
<212> TYPE: DNA
<213> ORGANISM: Artificial Sequence
<220> FEATURE:
<223> OTHER INFORMATION: ATL-1 primer-F

<400> SEQUENCE: 5
gaagatctat ggctaagagc cgcaggga                                         28

<210> SEQ ID NO 6
<211> LENGTH: 30
<212> TYPE: DNA
<213> ORGANISM: Artificial Sequence
<220> FEATURE:
<223> OTHER INFORMATION: ATL-1 primer-R

<400> SEQUENCE: 6
acgcgtcgac ttaaattttc ttcttttccg                                       30

<210> SEQ ID NO 7
<211> LENGTH: 33
<212> TYPE: DNA
<213> ORGANISM: Artificial Sequence
<220> FEATURE:
<223> OTHER INFORMATION: ATL-1 mutation-F

<400> SEQUENCE: 7
ctgatatttc ttgttcaaga ctggagtttc cca                                   33

<210> SEQ ID NO 8
<211> LENGTH: 33
<212> TYPE: DNA
<213> ORGANISM: Artificial Sequence
<220> FEATURE:
<223> OTHER INFORMATION: ATL-1 mutation-R

<400> SEQUENCE: 8
tgggaaactc cagtcttgaa caagaaatat cag                                   33
```